(12) United States Patent
Masaki et al.

(10) Patent No.: US 7,468,792 B2
(45) Date of Patent: Dec. 23, 2008

(54) EVALUATION APPARATUS AND EVALUATION METHOD

(75) Inventors: Yuichi Masaki, Kawasaki (JP); Yutaka Akino, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/959,810

(22) Filed: Dec. 19, 2007

(65) Prior Publication Data

US 2008/0100838 A1 May 1, 2008

Related U.S. Application Data

(63) Continuation of application No. 11/083,976, filed on Mar. 21, 2005, now Pat. No. 7,333,196.

(30) Foreign Application Priority Data

Mar. 22, 2004 (JP) ............................ 2004-082930

(51) Int. Cl.
*G01J 4/00* (2006.01)
*G01B 9/02* (2006.01)
(52) U.S. Cl. ...................... 356/326; 356/456
(58) Field of Classification Search ......... 356/300–334, 356/364–370, 450–456
See application file for complete search history.

(56) References Cited

U.S. PATENT DOCUMENTS

| | | | |
|---|---|---|---|
| 5,294,796 A * | 3/1994 | Fee ........................... | 250/338.5 |
| 5,347,475 A | 9/1994 | Taylor et al. ............ | 364/571.01 |
| 5,371,037 A * | 12/1994 | Yonehara .................... | 438/459 |
| 5,371,358 A * | 12/1994 | Chang et al. ................. | 250/226 |
| 6,040,191 A * | 3/2000 | Grow .......................... | 506/12 |
| 6,088,100 A * | 7/2000 | Brenan et al. ............... | 356/456 |
| 6,150,031 A | 11/2000 | Yonehara .................... | 428/446 |
| 6,240,312 B1 | 5/2001 | Alfano et al. ............... | 600/476 |
| 6,587,703 B2 | 7/2003 | Cheng et al. ................ | 600/310 |
| 6,744,046 B2 * | 6/2004 | Valaskovic et al. .......... | 250/288 |
| 6,838,243 B2 | 1/2005 | Lai et al. ....................... | 435/6 |
| 6,870,616 B2 * | 3/2005 | Jung et al. ................... | 356/326 |
| 7,106,425 B1 * | 9/2006 | Bultman et al. ............... | 356/73 |
| 2005/0007603 A1 | 1/2005 | Arieli et al. ................. | 356/601 |

FOREIGN PATENT DOCUMENTS

| | | |
|---|---|---|
| JP | 5-21338 | 1/1993 |
| JP | 2000-314612 | 11/2000 |

* cited by examiner

*Primary Examiner*—L. G Lauchman
*Assistant Examiner*—Jarreas C Underwood
(74) *Attorney, Agent, or Firm*—Fitzpatrick, Cella, Harper & Scinto

(57) ABSTRACT

An evaluation apparatus which evaluates a sample. The apparatus includes a light source which irradiates the sample with light, an imaging spectrometer which spectroscopically measures light reflected by the sample and senses an image, a first calculator which obtains amplitude information on an amplitude of a spectral reflectance of the sample based on the image sensed by the imaging spectrometer within a predetermined wavelength range of spectral reflectance spectra obtained by the spectrometer, a memory which holds in advance relationship information representing a relationship between the amplitude information of the spectral reflectance and an absorption coefficient, and a second calculator which obtains an absorption coefficient of the sample based on the amplitude information obtained by the first calculator and the relationship information held in the memory.

10 Claims, 12 Drawing Sheets

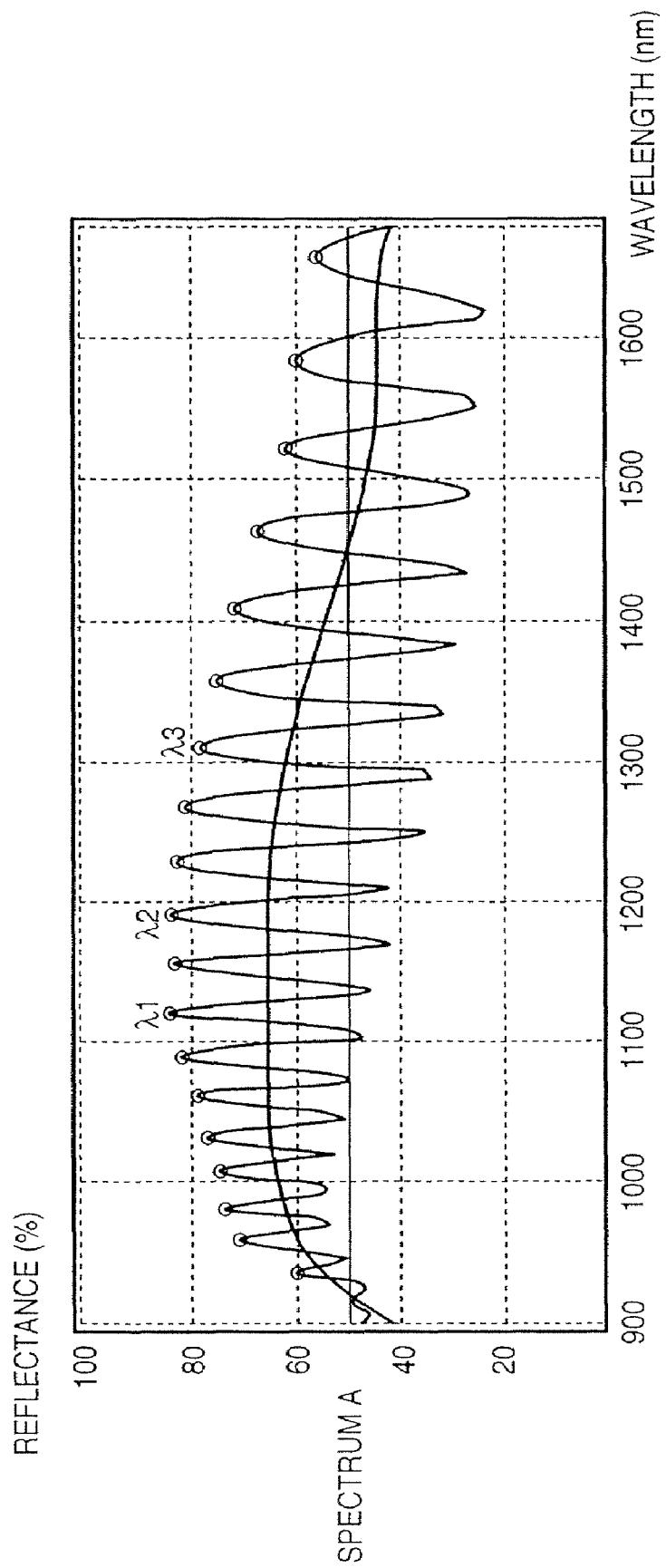

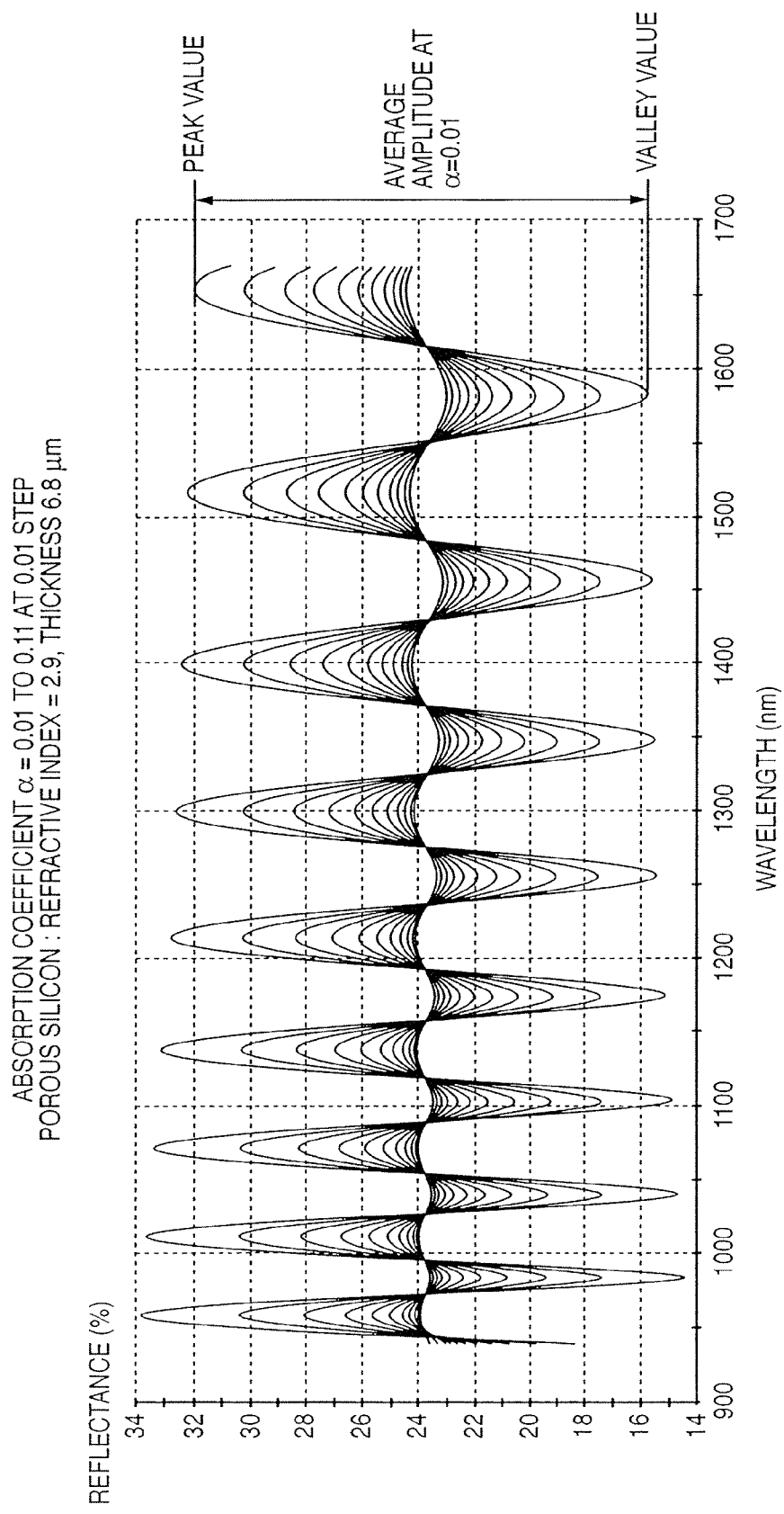

F I G. 7
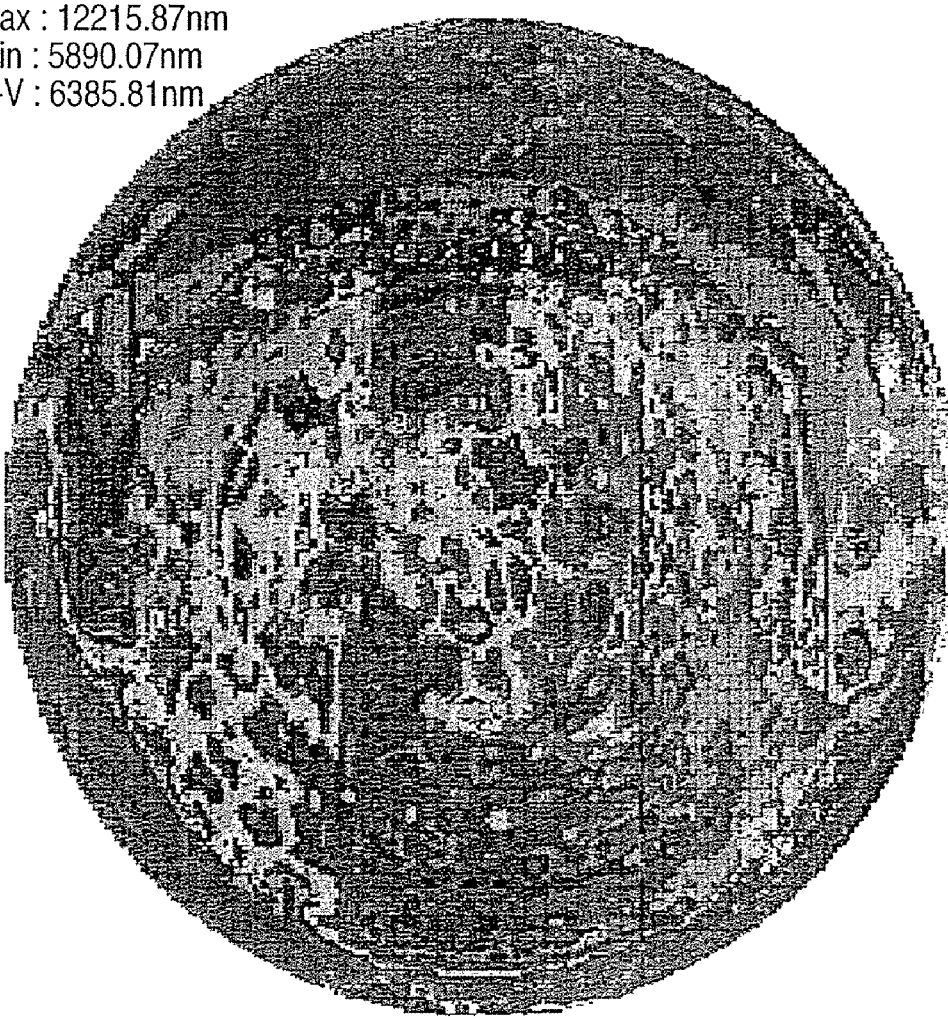

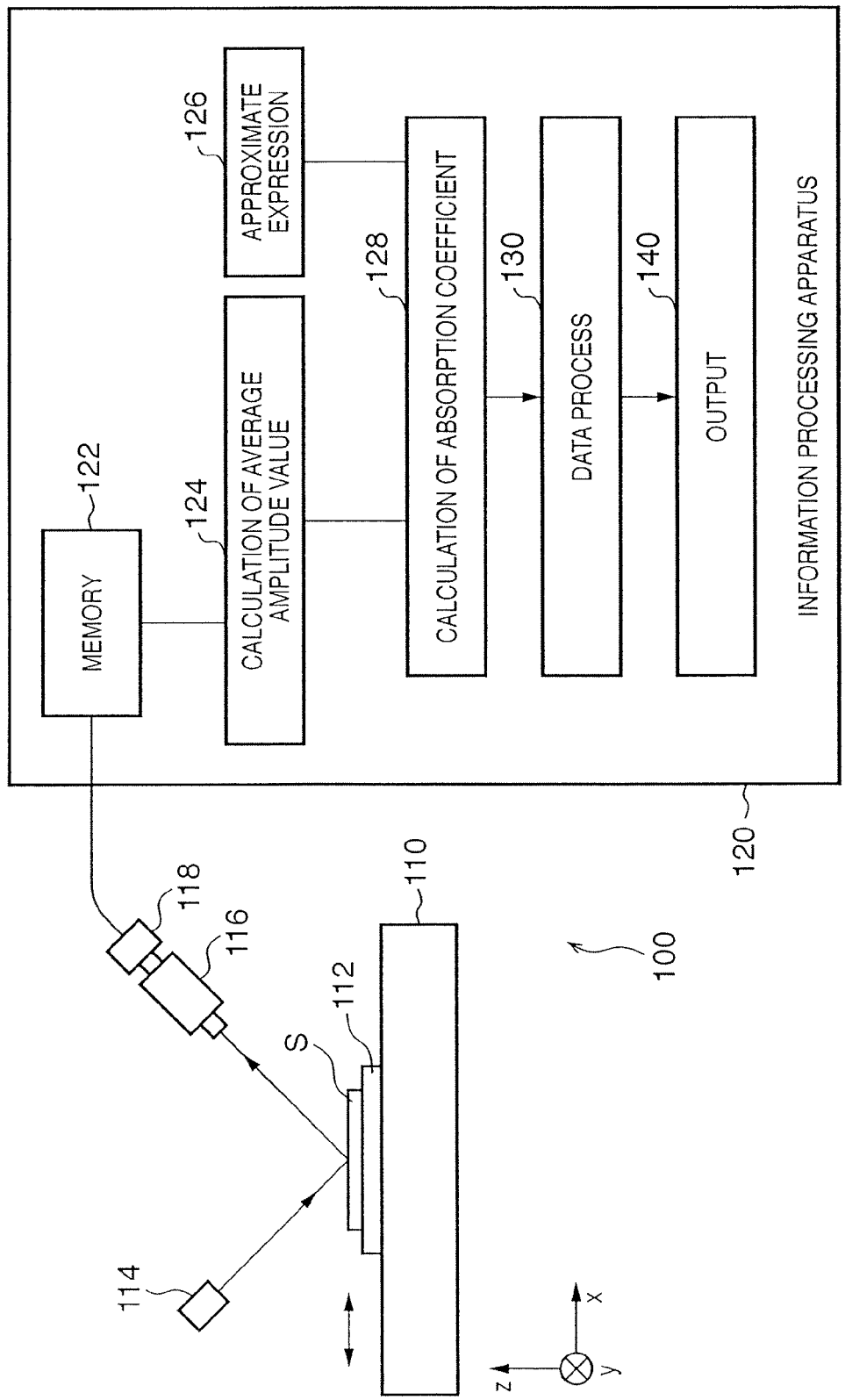

EVALUATION APPARATUS AND EVALUATION METHOD

This application is a continuation application of copending U.S. patent application Ser. No. 11/083,976, filed Mar. 21, 2005.

FIELD OF THE INVENTION

The present invention relates to an evaluation apparatus and an evaluation method, which evaluate a sample.

BACKGROUND OF THE INVENTION

The manufacture of an SOI (Silicon On Insulator or Semiconductor On Insulator) substrate utilizes a porous layer. According to an SOI substrate manufacturing method using a porous layer (see, e.g., Japanese Patent Laid-Open No. 5-21338), for example, a porous layer is formed on a seed substrate, and a semiconductor layer and an insulating layer are formed on the porous layer, fabricating a first substrate. The insulating layer side of the first substrate is bonded to a second substrate (handle substrate), fabricating a bonded substrate. After that, the bonded substrate is split into two substrates at the porous layer. As a result, the insulating layer and semiconductor layer on the seed substrate are transferred onto the handle substrate, obtaining an SOI substrate. This method is known as an ELTRAN method (ELTRAN is a registered trademark).

In the manufacture of an SOI substrate, the porous layer is used to form a semiconductor layer (e.g., an epitaxially grown layer) on it and by splitting a bonded substrate, and thus management of the quality of the porous layer is important. As a method of evaluating the characteristics of a porous material, a gas absorption method is known. However, this method takes a long time for sample preparations, such as degassing and temperature setting, and exhibits low evaluation efficiency.

A technique of measuring the thickness of a light transmitting film is disclosed in Japanese Patent Laid-Open No. 2000-314612. However, the technique in Japanese Patent Laid-Open No. 2000-314612 is irrelevant to the measurement of the quality.

SUMMARY OF THE INVENTION

The present invention has been made in consideration of the above situation, and has as its object to provide an evaluation apparatus and an evaluation method capable of quickly evaluating, e.g., the features of a sample.

According to the present invention, an evaluation apparatus, which evaluates a sample, comprises a light source which irradiates the sample with light, an imaging spectrometer which spectroscopically measures light reflected by the sample and senses an image, a first calculator which obtains amplitude information on an amplitude of a spectral reflectance of the sample based on the image sensed by the imaging spectrometer, a memory which holds in advance relationship information representing a relationship between the amplitude information of the spectral reflectance and an absorption coefficient, and a second calculator which obtains an absorption coefficient of the sample based on the amplitude information obtained by the first calculator and the relationship information held in the memory.

According to a preferred aspect of the present invention, the amplitude information may include an average amplitude of the spectral reflectance.

According to another preferred aspect of the present invention, the relationship information may include an approximate expression representing the relationship between the amplitude information of the spectral reflectance and the absorption coefficient.

According to still another preferred aspect of the present invention, the relationship information may include information representing a relationship between amplitude information of a spectral reflectance of a sample having a porous layer and an absorption coefficient of the porous layer.

According to still another preferred aspect of the present invention, the evaluation apparatus may further comprise an outputting unit which outputs the absorption coefficient obtained by the second calculator.

According to still another preferred aspect of the present invention, the evaluation apparatus may further comprise a data processor which converts the absorption coefficient obtained by the second calculator into a gradation value and maps the gradation value in a two-dimensional space to generate an image representing an evaluation result, and an outputting unit which outputs the image obtained by the data processor.

According to the second aspect of the present invention, an evaluation method of evaluating a sample comprises an imaging spectrometry step of spectroscopically measuring light reflected by the sample irradiated with light and sensing an image, a first calculation step of obtaining amplitude information on an amplitude of a spectral reflectance of the sample based on the image sensed in the imaging spectrometry step, and a second calculation step of obtaining an absorption coefficient of the sample based on the amplitude information obtained in the first calculation step, and relationship information which is held in a memory in advance and represents a relationship value between the amplitude information of the spectral reflectance and an absorption coefficient.

According to the present invention, for example, the features of a sample can be quickly evaluated.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 2A and 2B are graphs showing two spectra (spectra A and B) for the spectral reflectance obtained from one substrate having a porous layer by using a spectrometer;

FIG. 3 is a graph showing a theoretical spectral reflectance spectrum using the absorption coefficient of the porous layer as a parameter;

FIG. 7 is a view showing the results of mapping the thickness of the porous layer of the anodized sample in the two-dimensional space;

FIG. 11 is a view showing the schematic arrangement of an evaluation apparatus according to a preferred embodiment of the present invention.

DETAILED DESCRIPTION OF THE PREFERRED EMBODIMENT

A preferred embodiment of the present invention will be described below with reference to the accompanying drawings.

FIGS. 1A to 1F are sectional views schematically showing an SOI substrate manufacturing method. In the step shown in FIG. 1A, a semiconductor substrate (seed substrate) 11, such as a p-type single crystal silicon substrate, is prepared, and a porous semiconductor layer 12 is formed on the major surface of the substrate 11. The porous semiconductor layer 12 is formed on a surface facing a negative electrode by, for example, dipping the semiconductor substrate 11 into an HF (hydrogen fluoride) containing solution and supplying a current to the semiconductor substrate 11.

Figure 1A:
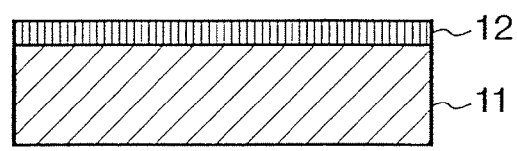
FIGS. 1A to 1F are sectional views schematically showing an SOI substrate manufacturing method.
Figure 1B:
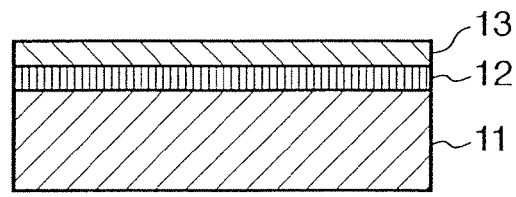

In the step shown in FIG. 1B, a semiconductor layer 13 is formed on the porous semiconductor layer 12. The semiconductor layer 13 is typically formed by epitaxially growing single crystal silicon on the porous single crystal semiconductor layer 12.

Figure 1C:
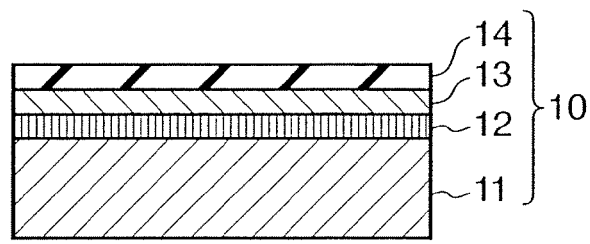

In the step shown in FIG. 1C, an insulating layer 14, such as an $SiO_2$ layer, is formed on the semiconductor layer 13 by thermal oxidation, or the like, obtaining a first substrate 10.

Figure 1D:
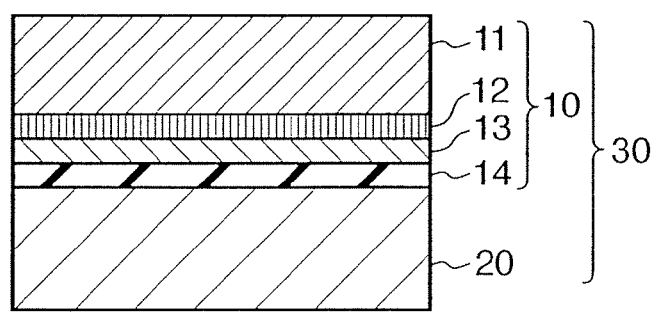

In the step shown in FIG. 1D, the surface of the first substrate 10 on the insulating layer 14 side is bonded to a second substrate (handle substrate) 20, forming a bonded substrate 30. When an insulating substrate, e.g., a substrate having an insulating layer thereon or a substrate formed of an insulator is adopted as the second substrate 20, the step shown in FIG. 1C can also be omitted.

Figure 1E:
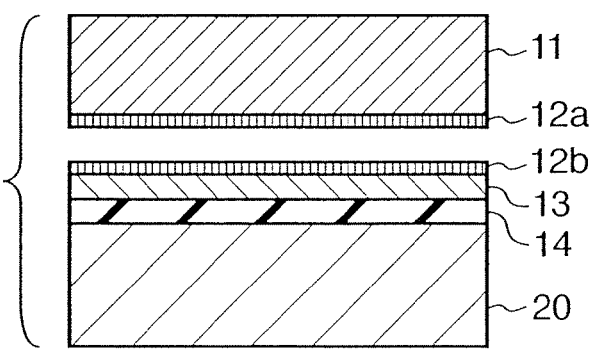

In the step shown in FIG. 1E, the bonded substrate 30 is split into two substrates by using the porous layer 12 as a separation layer. Splitting is done by, e.g., inserting or injecting a solid member or fluid into or around the porous layer 12. A method utilizing water as the fluid is an application of a water jet method.

Figure 1F:
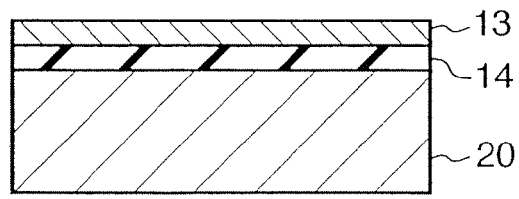

In the step shown in FIG. 1F, a porous layer 12b remaining on the major surface of the second substrate 20 after splitting is removed. Accordingly, an SOI (Silicon On Insulator or Semiconductor On Insulator) substrate, having the semiconductor layer (SOI layer) 13 on the insulating layer 14 serving as a buried insulating layer, is formed.

In the SOI substrate manufacturing method, the porous layer 12 is formed on the major surface of the semiconductor substrate 11 in the step shown in FIG. 1A. In the step shown in FIG. 1E, the residual porous layer 12a appears on the major surface of the semiconductor substrate (seed substrate) 11, and the residual porous layer 12b appears on the second substrate (handle substrate) 20. By evaluating the quality of the porous layer 12, the porous layer formation process (anodizing process)) shown in FIG. 1A can be optimized, and a failure in this process can be analyzed. Also, by evaluating the qualities of the residual porous layers 12a and 12b, the splitting process (separation process) shown in FIG. 1E can be optimized, and a failure in this process can be analyzed.

The quality of the porous layer is evaluated as absorption coefficients. The distribution of absorption coefficients (e.g., in plane distribution or inter substrate distribution) reflects the distribution of pore diameters of a porous layer formed in the step shown in FIG. 1A, and is effective for optimizing and managing the step. Separation scars which appear on the porous layer 12a remaining on the semiconductor substrate 11 and the porous layer 12b remaining on the second substrate 20 in the step shown in FIG. 1E can be observed as the distribution of absorption coefficients, and the absorption coefficient is effective for optimizing and managing this step.

Figure 2B:
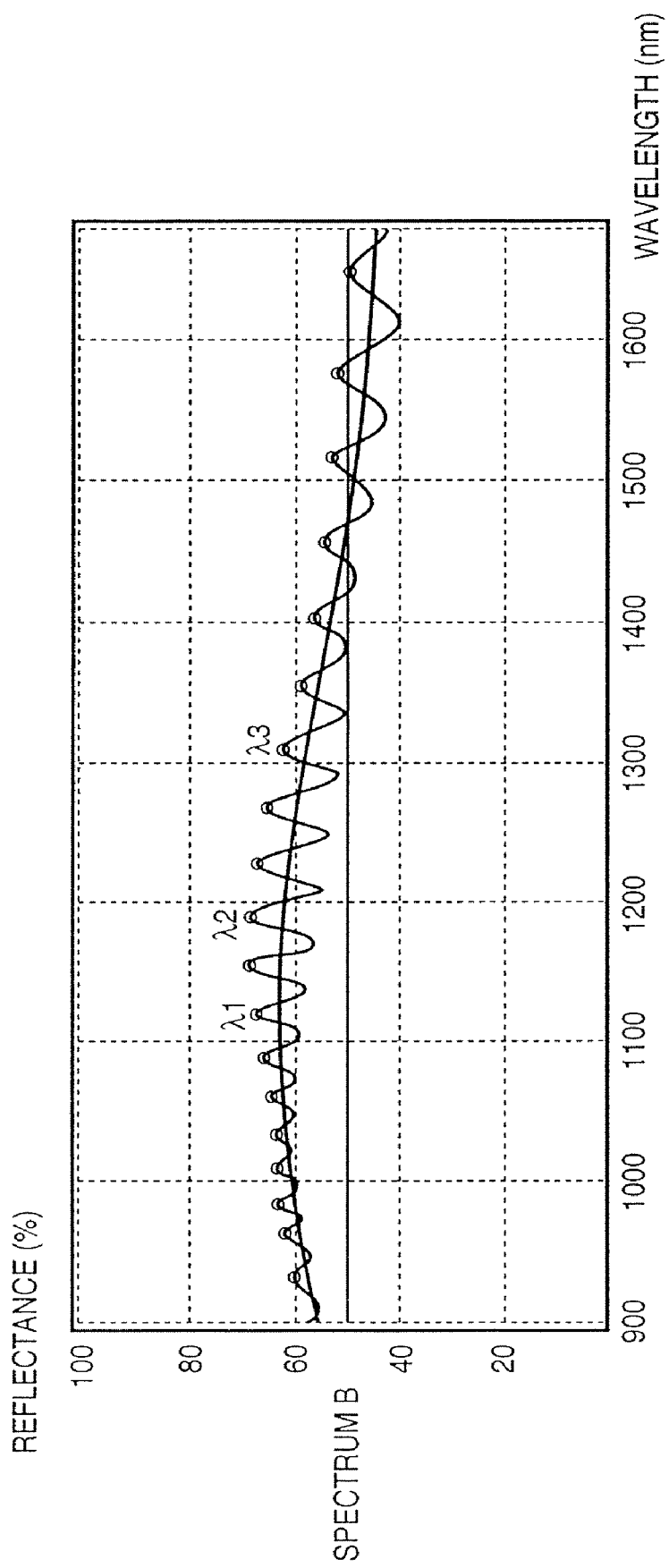

A principle for evaluating the absorption coefficient of a porous layer will be explained. FIGS. 2A and 2B are graphs showing spectra A and B for the spectral reflectance obtained from one substrate having a porous layer by using a spectrometer (ImSpector N17 (trade name) available from Kawatetsu Techno-Research). Spectra A and B are different in amplitude.

The thickness of the porous layer can be calculated based on three peak wavelengths $\lambda 1$, $\lambda 2$, and $\lambda 3$ in accordance with equation (1):

$$n \cdot d = m \cdot \lambda 1/2 = (m-3)\lambda 2/2 = (m-6)\lambda 3/2 \qquad (1)$$

In spectra A and B in FIGS. 2A and 2B, $\lambda 1=1,090$ nm, $\lambda 2=1,190$ nm, and $\lambda 3=1,310$ nm, the order m=36 for the index n of refraction=2.9, and the thickness d=about 6,770 nm. Spectra A and B in FIGS. 2A and 2B have the same peak wavelength, and the same thickness is obtained based on spectra A and B. Hence, the difference in the amplitude of the reflectance between spectra A and B is irrelevant to the thickness, and depends on the quality.

When light is vertically incident on a thin film having the index n of refraction and the physical thickness d, the characteristic matrix of the thin film is given by equation (2):

$$M = \begin{pmatrix} \cos\delta & i \cdot \sin\delta \\ i \cdot n \cdot \sin\delta & \cos\delta \end{pmatrix} = \begin{pmatrix} m_{11} & i \cdot m_{12} \\ i \cdot m_{21} & m_{22} \end{pmatrix} \qquad (2)$$

where $\delta = (2\pi/\lambda) n \cdot d$.

When the thin film exhibits absorption, $N = n - i \cdot k$ is used instead of n in equation (2).

The characteristic matrix includes the imaginary number i, and is arranged using a hyperbolic function to obtain equation (3):

$$\cos(x-iy) = \cos x \times \cos hy + i \times \sin x \times \sin hy$$

$$\sin(x-iy) = \sin x \times \cos hy - i \times \cos x \times \sin hy$$

where $\cos hy = (e^x + e^{-y})/2$, $\sin hy = (e^x - e^{-y})/2$. (3)

A spectral reflectance when light having the wavelength $\lambda$ is vertically incident on a thin film of a single layer ($N = n - i \cdot k$, physical thickness d) exhibiting absorption on an absorption substrate ($N \cdot m = n \cdot m - i \cdot k \cdot m$) is calculated (incident medium $N_0 = n_0 - i k_0$).

$$x = (2\pi/\lambda) n \cdot d, \quad y = (2\pi/\lambda) k \cdot d \qquad (4)$$

The elements of characteristic matrix (2) are arranged into the real part and an imaginary part:

$$m_{11} = \cos\{2\pi(n-ik)d/\lambda\} \quad (5)$$
$$= \cos(x - iy)$$
$$= \cos x \cdot \cosh y + i\sin x \cdot \sinh y$$
$$= a + ib$$
$$= m_{22}$$
$$= g + ih$$

$$im_{12} = i(\sin x \cdot \cosh y - i\cos x \cdot \sinh y)/(n-ik) \quad (6)$$
$$= \{(n \cdot \cos x \cdot \sinh y - k \cdot \sin x \cdot \cosh y) +$$
$$i(n \cdot \sin x \cdot \cosh y + k \cdot \cos x \cdot \sinh y)\}/(n^2 + k^2)$$
$$= c + id$$

$$im_{21} = (n \cdot \cos x \cdot \sinh y + k \cdot \sin x \cdot \cosh y) + \quad (7)$$
$$i(n \cdot \sin x \cdot \cosh y - k \cdot \cos x \cdot \sinh y)$$
$$= e + if$$

where a to h are real numbers. Letting B and C be the amplitudes of a normalized electrical field magnetic field, respectively, $$\begin{pmatrix} B \\ C \end{pmatrix} = \begin{pmatrix} a+ib & c+id \\ e+if & g+ih \end{pmatrix} \begin{pmatrix} 1 \\ n_m - ik_m \end{pmatrix} \quad (8)$$
$$= \begin{pmatrix} a + n_m c + k_m d + i(b - k_m c + n_m d) \\ e + n_m g + k_m h + i(f - k_m g + n_m h) \end{pmatrix}.$$

An amplitude reflectance coefficient (Fresend coefficient) $\rho$ of the electrical field is $$\rho = \frac{BN_0 - C}{BN_0 + C} = \frac{Q_1 + iQ_2}{Q_3 + iQ_4} \quad (9)$$

where $$Q_1 = (a + n_m c + k_m d)n_0 + (b - k_m c + n_m d)k_0 - (e + n_m g + k_m h)$$
$$Q_2 = -(a + n_m c + k_m d)k_0 + (b - k_m c + n_m d)n_0 - (f - k_m g + n_m h)$$
$$Q_3 = (a + n_m c + k_m d)n_0 + (b - k_m c + n_m d)k_0 + (e + n_m g + k_m h)$$
$$Q_4 = -(a + n_m c + k_m d)k_0 + (b - k_m c + n_m d)n_0 + (f - k_m g + n_m h). \quad (10)$$

Hence, an energy reflectance R is $$R = \rho\rho^* = \frac{Q_1^2 + iQ_2^2}{Q_3^2 + iQ_4^2}. \quad (11)$$

By using the wavelength $\lambda$ as a variable, the spectral reflectance characteristic can be calculated.

FIG. 3 shows the results of simulating the spectral reflectance of a virtual sample in accordance with equations (1) to (11) at the wavelength $\lambda$ of 900 to 1,700 nm by changing an absorption coefficient a=4 pk/$\lambda$ of the porous layer 12 from 0.01 to 0.11 at 0.01 step for the virtual sample having the porous layer 12 (in this case, the refractive index=2.9 and the thickness=6.8 mm) on the p$^+$ silicon substrate (refractive index=3.5) 11.

Figure 4:
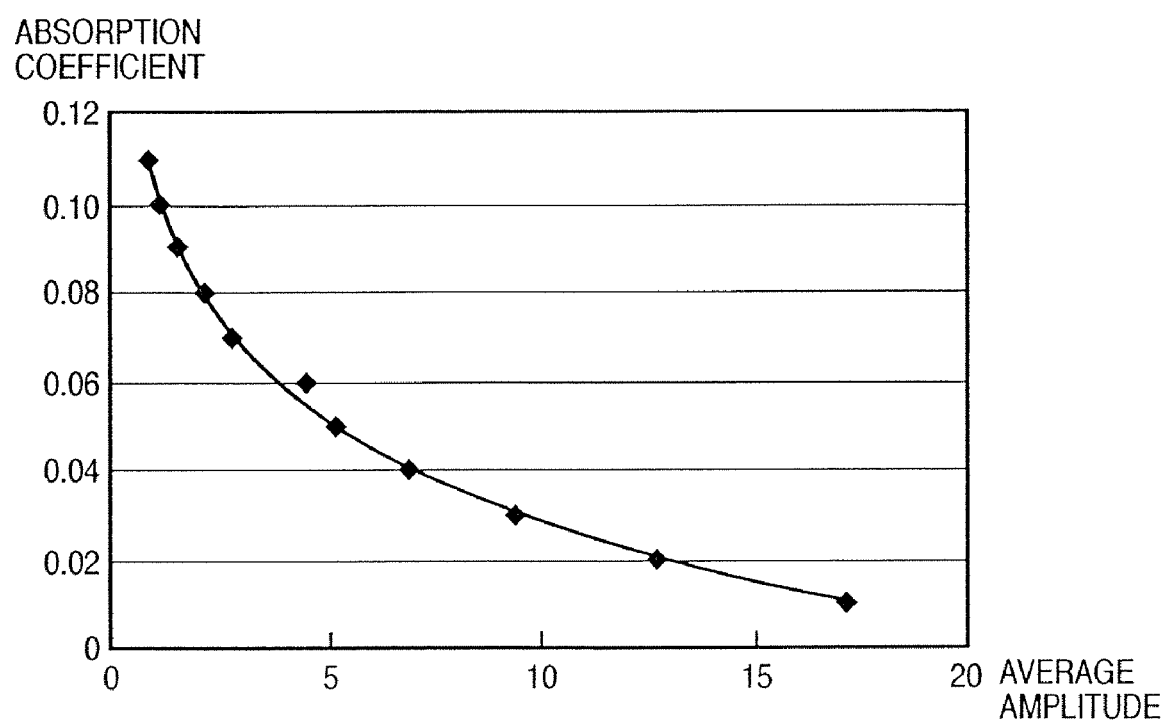
FIG. 4 is a graph showing the relationship between the absorption coefficient and an average amplitude calculated from the peak and valley values of the spectral reflectance spectrum in FIG. 3.

From the results shown in FIG. 3, the difference in amplitude between two spectra A and B in FIGS. 2A and 2B can be considered to derive from the difference in absorption coefficient. FIG. 4 is a graph showing the relationship between the absorption coefficient and an average amplitude calculated from the peak and valley values of the spectral reflectance spectrum in FIG. 3. The graph in FIG. 4 complies with equation (12):

$$\alpha = 0.033 \, \mathrm{Ln}(x) + 0.1043. \quad (12)$$

In the above manner, simulation is executed under conditions (e.g., the refractive index of the semiconductor substrate 11 and the refractive index and thickness of the porous layer 12) coincident with those of an object (e.g., the substrate shown in FIG. 1A) to be measured, thereby obtaining relationship information (e.g., approximate expression) representing the relationship between the average amplitude of the spectral reflectance and the absorption coefficient. An absorption coefficient representing the quality can be obtained based on the approximate expression and a spectrum waveform obtained by using a spectrometer.

FIG. 11 is a view showing the schematic arrangement of an evaluation apparatus complying with the above-described principle according to the preferred embodiment of the present invention. An evaluation apparatus 100 comprises a stage 112, which holds a substrate S serving as an object (sample) to be evaluated, a stage driving mechanism 110, which moves the stage 112 along the x axis, a line-shaped light source 114, which irradiates the substrate S with line shaped light (e.g., halogen light) elongated along the y-axis, a condensing optical system 116, which condenses interference light (reflected light) that is emitted by the line-shaped light source 114 and reflected by the substrate S, an imaging spectrometer 118, which spectroscopically measures interference light (reflected light) condensed by the condensing optical system 116 and senses an image, and an information processing apparatus (computer) 120, which processes the image sensed by the imaging spectrometer 118, to obtain an absorption coefficient serving as an evaluation index for the quality of a porous layer on the major surface of the substrate S.

The line-shaped light source 114 irradiates the substrate S with line-shaped light having a width (length along the y-axis) enough to cover the length of the substrate S along the y-axis. The stage driving mechanism 110 drives the stage 112 along the x-axis so as to scan the entire substrate S with line-shaped light. With this operation, the quality of the porous layer on the major surface of the substrate S can be measured for the entire substrate S.

The imaging spectrometer 118 spectroscopically measures interference light condensed by the condensing optical system 116 at a wavelength of, e.g., 900 nm to 1,700 nm, and senses an image from the spectroscopically measured light by an image sensing element such as a CCD. In this case, the imaging spectrometer 118 spectroscopically measures interference light so as to attain position information along the x-axis and spectrum information along the y-axis in a two-dimensional space defined by the x- and y-axes. An image sensed by the image sensing element is a set of spectra at points (points on lines along the y-axis) of line shaped light, and each spectrum pattern shows an interference waveform at each point. Spectrum information of the line-shaped light source 114 and the influence of variations in the measurement sensitivity of the image sensing element are removed from these interference waveforms, obtaining the reflectance of the substrate S at each wavelength for each point.

The information processing apparatus 120 comprises a memory 122, which stores an image obtained by the imaging spectrometer 118, a first calculator 124, which analyzes the spectrum of the image stored in the memory 122 to calculate the average amplitude of the spectral reflectance of the substrate S, a memory 126, which stores an approximate expression representatively shown in FIG. 4 (approximate expression representing the relationship between the average amplitude and the absorption coefficient) as relationship information (information representing the relationship between the average amplitude and the absorption coefficient), a second calculator 128, which calculates the absorption coefficient of the porous layer on the major surface of the substrate S based on the average amplitude calculated by the first calculator 124 and the approximate expression stored in the memory 126, a data processor 130, which generates data to be output (e.g., to be displayed) based on the absorption coefficient obtained by the calculator 128, and an outputting unit 140, which outputs the absorption coefficient calculated by the calculator 128 and/or the data generated by the data processor 130. The outputting unit 140 includes, e.g., all or some of a display (monitor), printer, communication line, and memory.

The data processor 130 can map, e.g., absorption coefficients at all points (sampling points) on the major surface of the substrate S in the two-dimensional space. At this time, absorption coefficients can be substituted with gradation values within a range of the average value of the absorption coefficient $\pm \sigma$, and mapped as a color gradation in the two-dimensional space. By displaying data generated in this way on the monitor, the evaluator can visually recognize the distribution of absorption coefficients immediately. For example, when one point on an 8" substrate S has an area of 40 μm in length and 80 mm in breadth, measurement data (absorption coefficients) at about 100,000 points can be obtained on the entire substrate S.

As described above, absorption coefficients can be attained from the entire substrate S by spectroscopically measuring interference light coming from a region irradiated with line-shaped light elongated in the y direction, while sequentially moving the substrate S in the x direction. Also, the substrate S is irradiated with light, light reflected by the substrate S is spectroscopically measured to sense an image, and the sensed image is processed to obtain an absorption coefficient. According to this method, a sample (substrate S) to be evaluated can be easily adjusted to rapidly attain an evaluation result.

In the above arrangement, the average amplitude of the spectral reflectance is calculated, and the absorption coefficient is obtained based on the average amplitude. However, the average value of the spectral reflectance need not always be used as far as the spectral reflectance is correlated with the absorption coefficient.

Several examples will be illustratively explained for a concrete understanding of the present invention.

EXAMPLE 1

A silicon wafer having a resistivity of 15 mΩ·cm was set between a Pt negative electrode and a Pt positive electrode within a vessel of a 42% hydrogen fluoride solution. A 5-A DC constant current was supplied for two minutes, then the current was increased to 9 A, supplied for one minute, and stopped (FIG. 1A). Two porous layers 12 having different porosities were formed on a surface of the substrate 11 that faced the negative electrode. The substrate 11 was rinsed for three minutes with an aqueous 10% IPA (isopropyl alcohol) solution, cleaned with pure water for five minutes, and spin-dried (at 1,500 rpm for two minutes).

Figure 5:
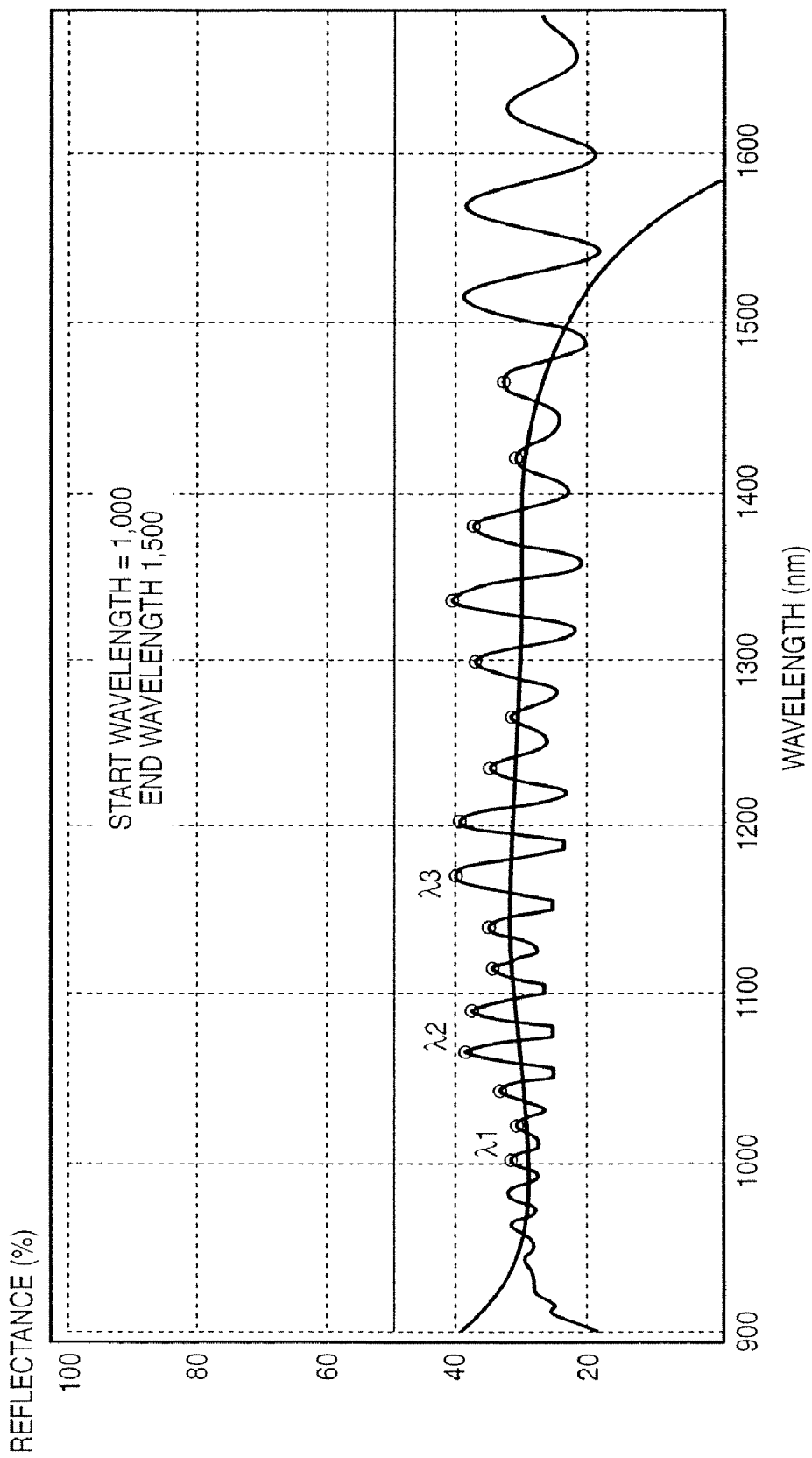
FIG. 5 is a graph showing measured spectral reflectance spectra at arbitrary points of a sample having a porous layer of a two-layered structure.
Figure 6:
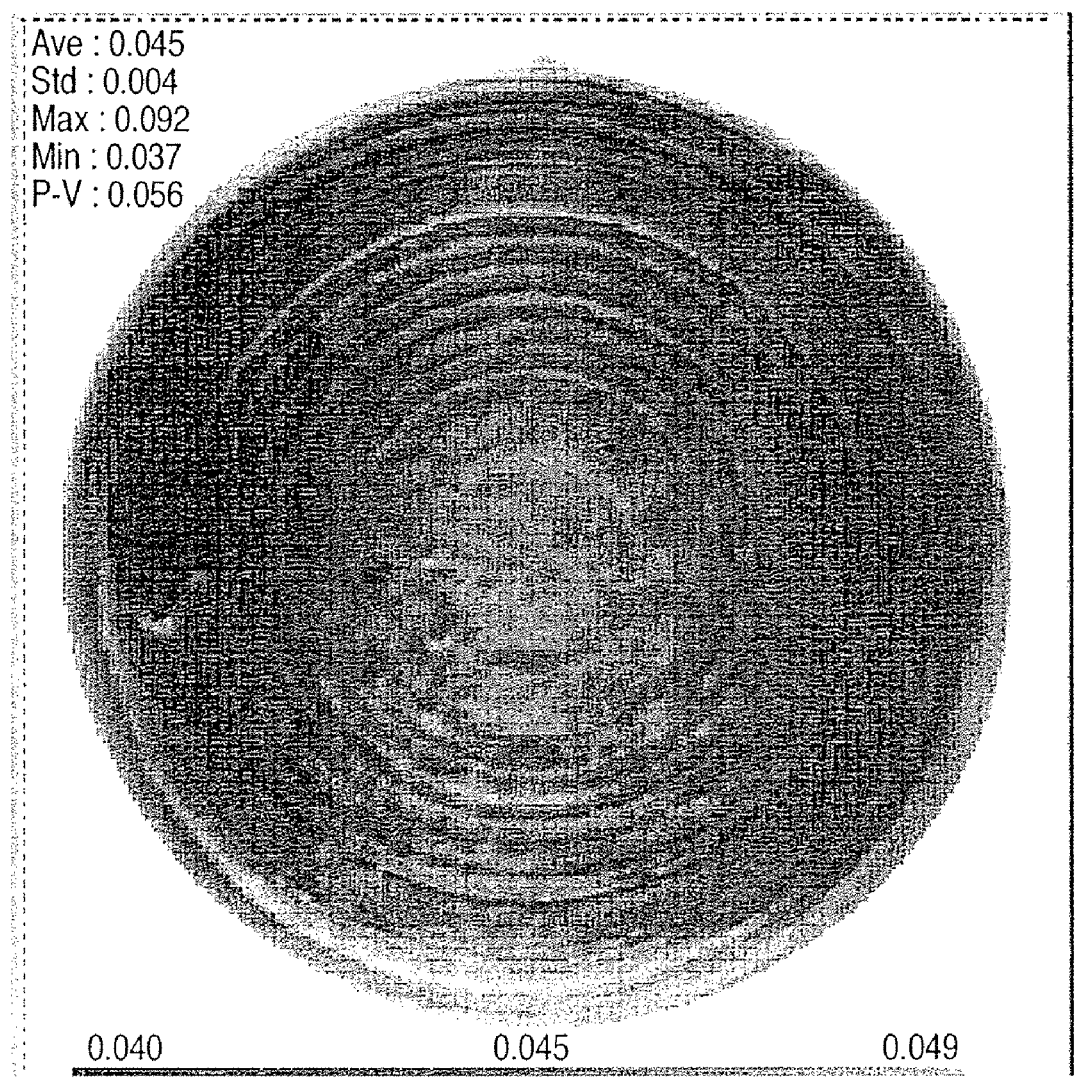
FIG. 6 is a view showing the results of mapping the absorption coefficient of the porous layer of the anodized sample in the two-dimensional space.

The quality of the obtained porous layer 12 on the substrate 11 prepared in this way was measured using the evaluation apparatus 100 shown in FIG. 11. FIG. 5 shows spectral reflectance spectra at arbitrary points. The amplitude average of the peak and valley values of the reflectance is 7% within a range of 1,000 nm to 1,500 nm, and the absorption coefficient is 0.04 from the approximate expression shown in FIG. 4. The same data process was performed at all points, and color gradation was determined within a range of the average $\pm \sigma$ and underwent a mapping process. FIG. 6 is a view showing an image obtained by the mapping process. A concentric distribution can be confirmed at absorption coefficients shown in FIG. 6. This distribution is considered to derive from the fact that the absorption coefficient is proportional to the boron concentration of the substrate 11. FIG. 7 is a view showing an image obtained by performing a mapping process for the thickness of the porous layer 12 of the same substrate 11.

EXAMPLE 2

After the end of the steps described in example 1, the substrate was heated in an oxygen atmosphere at 400° C. for 1 h to form an oxide film on the major surface of the porous layer 12. The major surface was cleaned with 1% dilute hydrofluoric acid, washed with water, and dried, and then a silicon layer 13 was epitaxially grown by 280 nm (FIG. 1B). The substrate was processed in an oxygen atmosphere at 800° C. for 15 min to form a 100-nm $SiO_2$ layer 14 on the major surface, obtaining a first substrate 10.

The first substrate 10 was bonded to a p$^-$ wafer serving as a second substrate 20 having a 50-nm $SiO_2$ film on the major surface, and bonding annealing was executed at 1,000° C. for 120 min, obtaining a bonded substrate 30 (FIG. 1C).

While the bonded substrate 30 was rotated, the water pressure was increased up to 20 MPa at maximum by a water jet about 0.1 mm in diameter, and the water jet nozzle was moved from a position at which the nozzle was directed to the peripheral portion of the bonded substrate 30 to a position at which the nozzle was directed to the central portion, thereby splitting the bonded substrate 30 into two substrates (FIG. 1D).

Figure 8:
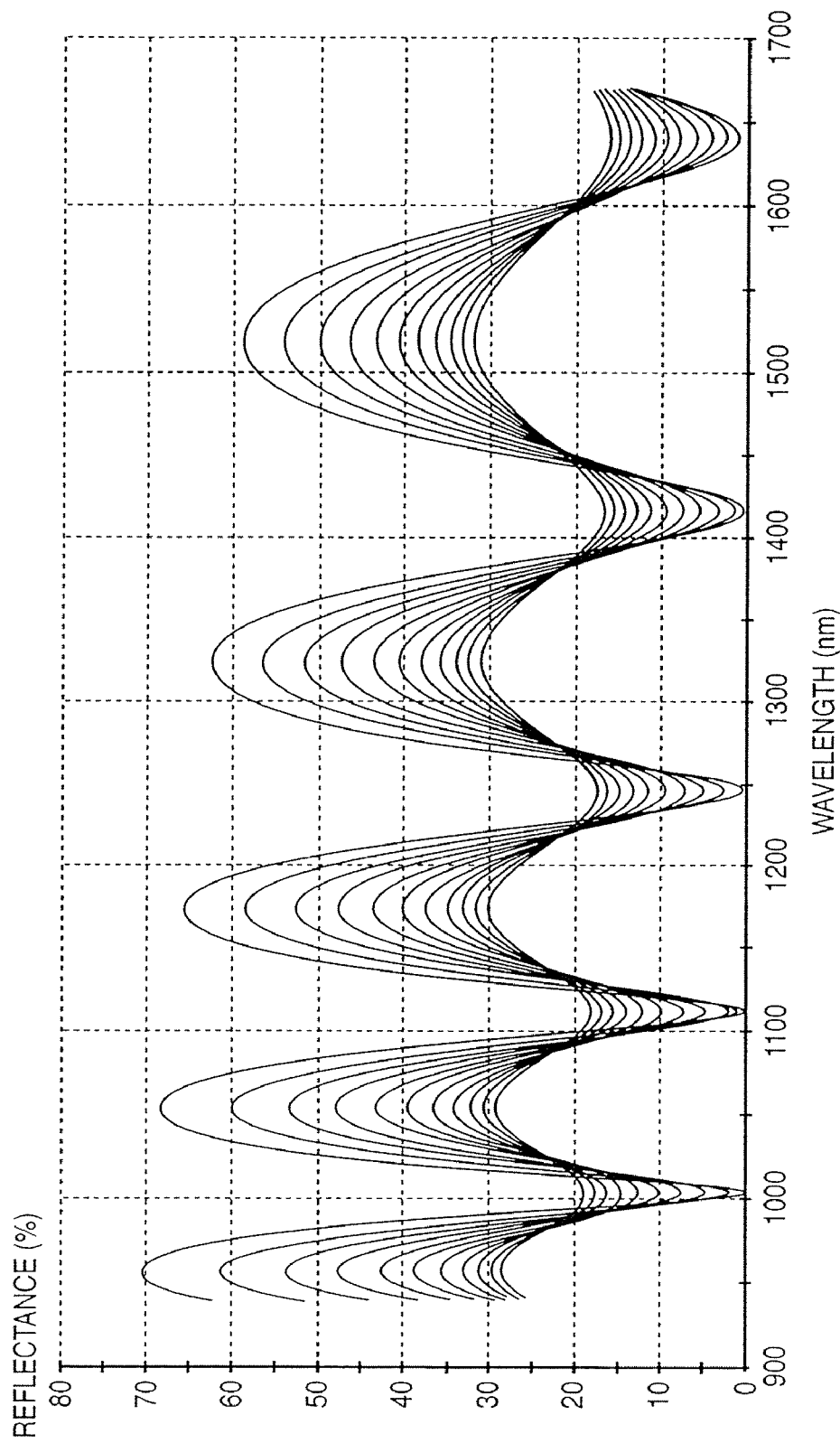
FIG. 8 is a graph showing a theoretical spectral reflectance spectrum using as a parameter the absorption coefficient of a porous layer remaining on the split sample.

After that, the split p$^-$ substrate was evaluated using the evaluation apparatus 100 shown in FIG. 11. An approximate expression in this case was obtained on the assumption that an $SiO_2$ layer 14 having a thickness of 150 nm and a refractive index of 1.46 existed on the silicon wafer 20, a single crystal silicon layer (SOI layer) 13 having a thickness of 50 nm and a refractive index of 3.5 existed on the $SiO_2$ layer 14, and a residual porous layer 12b having a thickness of 5 mm and a refractive index of 2.9 existed on the silicon layer 13. Under this condition, a theoretical reflectance was obtained by simulation at a wavelength of 900 nm to 1,650 nm by using the absorption coefficient as a parameter. FIG. 8 shows the relationship between the average amplitude and absorption coefficient obtained by this simulation. The approximate expression was:

$$\alpha = -0.0584 \, Ln(x) + 0.2587.$$

Figure 9:
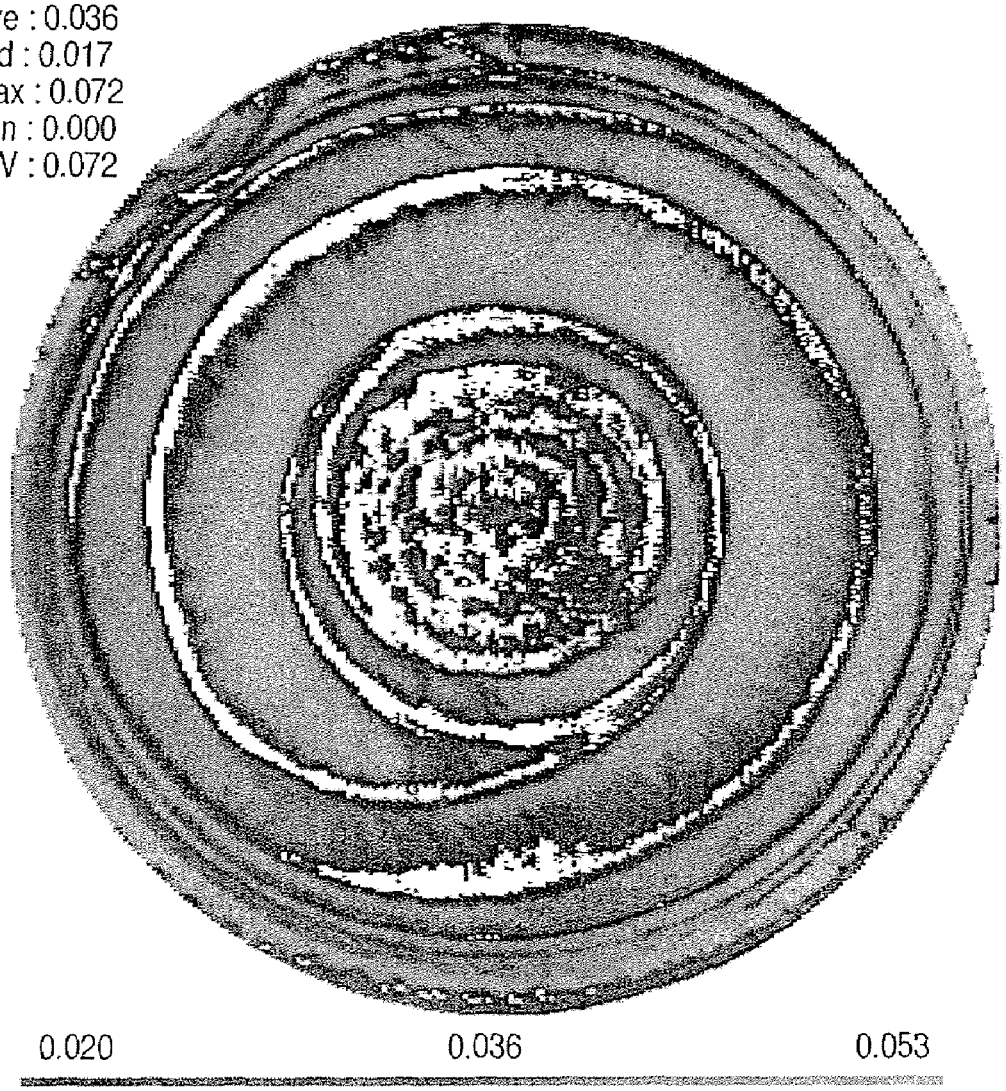
FIG. 9 is a view showing the results of mapping the absorption coefficient of the porous layer remaining on the split sample in the two-dimensional space.

FIG. 9 is a view showing an image obtained by the mapping process. In FIG. 9, a distribution spiraling toward the center can be confirmed, and splitting scars (separation scars) can be observed at the interface between the first and second layers of the porous layer. Since separation scars change depending on the formation conditions of the porous layer, the splitting step (separation step) shown in FIG. 1E can be managed by comparing sampled separation scars and normal separation scars on the substrate.

EXAMPLE 3

Figure 10:
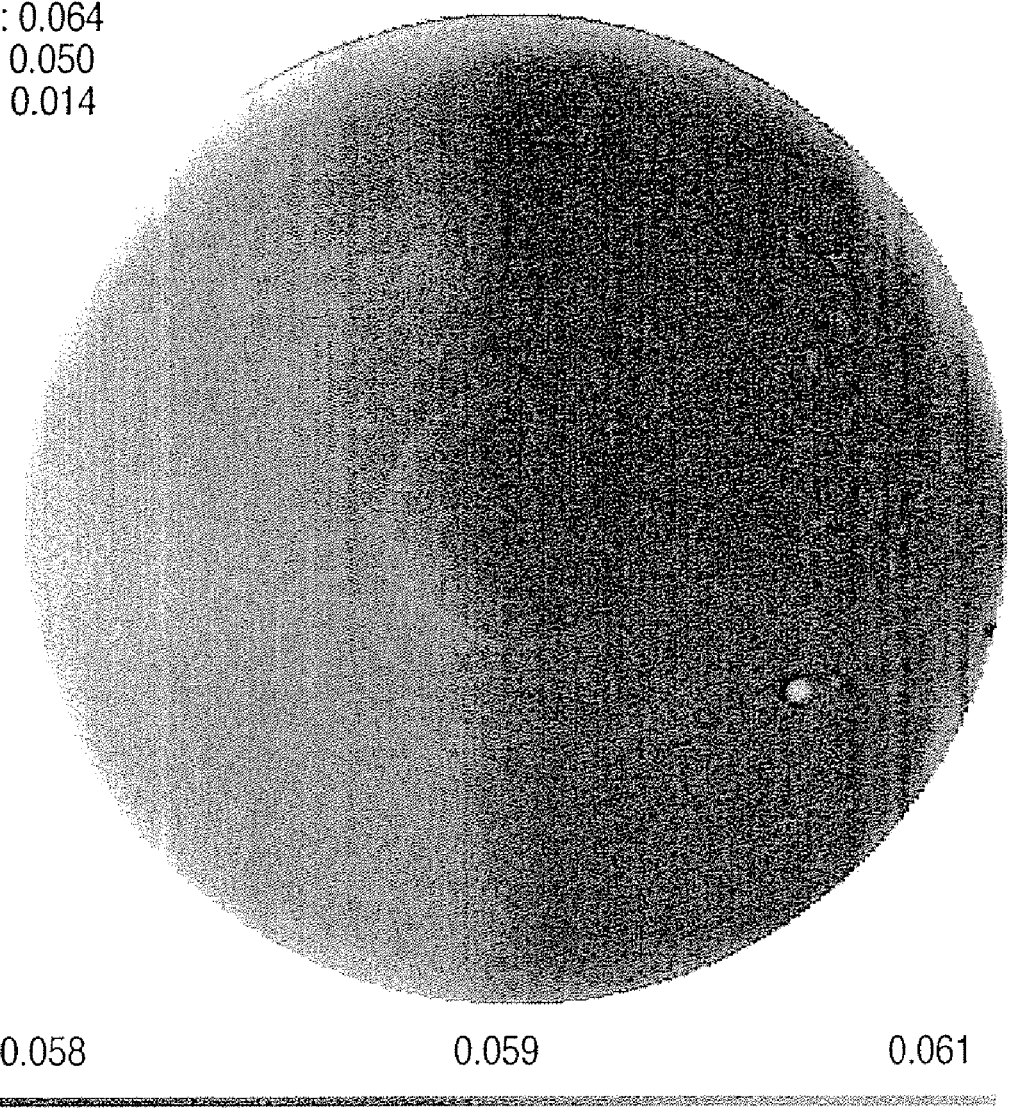
FIG. 10 is a view showing the results of mapping in the two-dimensional space the absorption coefficient of a sample obtained by bonding the first and second substrates.

After the end of the bonding step (FIG. 1D) described in example 2, the bonded substrate 30 was evaluated using the evaluation apparatus 100 shown in FIG. 11 with the p⁻ substrate 20 facing up. At this time, mapping shown in FIG. 10 was obtained by temporarily applying the approximate expression used in example 2. In FIG. 10, a void was observed between the two bonded substrates. Such a bonded substrate on which a void is observed results in a defective SOI substrate, and should be rejected without proceeding to the subsequent step. In this example, the state of the bonded portion between the p⁻ substrate 20 and the first substrate 10 was evaluated.

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent application No. 2004-082930, filed on Mar. 22, 2004, the entire contents of which are hereby incorporated by reference herein.

What is claimed is:

1. An evaluation apparatus which evaluates a sample, the apparatus comprising:
    a light source which irradiates the sample with light;
    an imaging spectrometer which spectroscopically measures light reflected by the sample and senses an image;
    a first calculator which obtains amplitude information on an amplitude of a spectral reflectance of the sample based on the image sensed by the imaging spectrometer within a predetermined wavelength range of spectral reflectance spectra obtained by the spectrometer;
    a memory which holds in advance relationship information representing a relationship between the amplitude information of the spectral reflectance and an absorption coefficient; and
    a second calculator which obtains an absorption coefficient of the sample based on the amplitude information obtained by the first calculator and the relationship information held in the memory;
    wherein the relationship information includes information representing a relationship between amplitude information of a spectral reflectance of a sample having a porous layer and an absorption coefficient of the porous layer.

2. The apparatus according to claim 1, wherein the amplitude information includes an average amplitude of the spectral reflectance.

3. The apparatus according to claim 1, wherein the relationship information includes an approximate expression representing the relationship between the amplitude information of the spectral reflectance and the absorption coefficient.

4. The apparatus according to claim 1, further comprising an outputting unit which outputs the absorption coefficient obtained by the second calculator.

5. The apparatus according to claim 1, further comprising:
    a data processor which converts the absorption coefficient obtained by the second calculator into a gradation value and maps the gradation value in a two-dimensional space to generate an image representing an evaluation result; and
    an outputting unit which outputs the image obtained by the data processor.

6. An evaluation method of evaluating a sample, the method comprising:
    an imaging spectrometry step of spectroscopically measuring light reflected by the sample irradiated with light and sensing an image;
    a first calculation step of obtaining amplitude information on an amplitude of a spectral reflectance of the sample based on the image sensed in the imaging spectrometry step within a predetermined wavelength range of spectral reflectance spectra obtained in the spectrometry step; and
    a second calculation step of obtaining an absorption coefficient of the sample based on the amplitude information obtained in the first calculation step, and relationship information which is held in a memory in advance and represents a relationship value between the amplitude information of the spectral reflectance and an absorption coefficient;
    wherein the relationship information includes information representing a relationship between amplitude information of a spectral reflectance of a sample having a porous layer and an absorption coefficient of the porous layer.

7. The method according to claim 6, wherein the amplitude information includes an average amplitude of the spectral reflectance.

8. The method according to claim 6, wherein the relationship information includes an approximate expression representing the relationship between the amplitude information of the spectral reflectance and the absorption coefficient.

9. The method according to claim 6, further comprising an outputting step of outputting the absorption coefficient obtained in the second calculation step.

10. The method according to claim 6, further comprising:
    a data processing step of converting the absorption coefficient obtained in the second calculation step into a gradation value and mapping the gradation value in a two-dimensional space to generate an image representing an evaluation result; and
    an outputting step of outputting the image obtained in the data processing step.

* * * * *